United States Patent [19]

Carter

[11] Patent Number: 5,712,257
[45] Date of Patent: Jan. 27, 1998

[54] TOPICALLY ACTIVE COMPOSITIONS OF MISMATCHED DSRNAS

[75] Inventor: William A. Carter, Birchrunville, Pa.

[73] Assignee: HEM Research, Inc., Philadelphia, Pa.

[21] Appl. No.: 447,427

[22] Filed: May 23, 1995

Related U.S. Application Data

[63] Continuation of Ser. No. 147,431, Nov. 5, 1993, abandoned, which is a continuation of Ser. No. 926,372, Aug. 10, 1992, abandoned, which is a continuation of Ser. No. 731,400, Jul. 17, 1991, abandoned, which is a continuation of Ser. No. 545,661, Jul. 2, 1990, abandoned, which is a continuation of Ser. No. 428,016, Oct. 26, 1989, abandoned, which is a continuation of Ser. No. 227,929, Aug. 3, 1988, abandoned, which is a continuation-in-part of Ser. No. 84,226, Aug. 12, 1987, abandoned.

[51] Int. Cl.$^6$ .......................... A61K 31/715; A61K 6/04; C07H 21/02
[52] U.S. Cl. .......................... 514/44; 536/23.1; 128/844; 514/934
[58] Field of Search ................ 514/44, 934; 128/844; 536/23.1

[56] References Cited

U.S. PATENT DOCUMENTS

| | | | |
|---|---|---|---|
| 4,020,183 | 4/1977 | Asculai et al. | 424/341 |
| 4,024,222 | 5/1977 | Ts'o et al. | 514/44 |
| 4,130,541 | 12/1978 | Ts'o et al. | 514/44 |
| 4,139,630 | 2/1979 | Asculai et al. | 514/461 |
| 4,283,393 | 8/1981 | Field et al. | 514/44 |
| 4,400,375 | 8/1983 | Douthart et al. | |
| 4,415,548 | 11/1983 | Reddy | 424/28 |
| 4,507,281 | 3/1985 | Asculai et al. | 424/85.7 |
| 4,795,744 | 1/1989 | Carter | 514/44 |
| 4,820,696 | 4/1989 | Carter | 514/44 |
| 4,945,082 | 7/1990 | Carter | 514/44 |
| 4,950,652 | 8/1990 | Carter | 514/44 |
| 4,963,532 | 10/1990 | Carter | 514/44 |
| 5,063,209 | 11/1991 | Carter | 514/44 |
| 5,091,374 | 2/1992 | Carter | 514/44 |
| 5,132,292 | 7/1992 | Carter | 514/44 |
| 5,258,364 | 11/1993 | Carter | 514/44 |
| 5,593,973 | 1/1997 | Carter | 514/44 |

FOREIGN PATENT DOCUMENTS

| | | |
|---|---|---|
| A- 213 912 | 3/1987 | European Pat. Off. |
| A-2 556 727 | 12/1983 | France . |
| A-1 230 065 | of 0000 | United Kingdom . |

OTHER PUBLICATIONS

Hicks et al, The Lancet, vol. II No. 8469/70, pp. 1422, 1423, Dec. 21/28, 1985.

Journal of Biological Response Modifiers, 4:495–502, 1985, Raven Press "Comparative Studies of Ampligen (Mismatched Double Stranded RNA) and Interferons", Carter et al.

Journal of Biological Response Modifiers 4:495–502, 1985, Raven Press "Preclinical Studies with Ampligen (Mismatched Double Stranded RNA)", Carter et al.

Primary Examiner—Gary L. Kunz
Attorney, Agent, or Firm—Nixon & Vanderhye

[57] ABSTRACT

Surfactant-stabilized ternary complexes of dsRNAs in topical pharmaceutical compositions, optionally also including a lymphokine and/or an inhibitor of reverse transcriptase, are applied topically to the affected or exposed area to treat or prevent viral infections, such as herpes virus, and other infectious conditions, particularly venereally transmitted pathogens. Ternary complexes of two strands of complementary RNA plus a compatible surfactant stabilized against temperature-associated enzymatic inactivation are described.

15 Claims, 1 Drawing Sheet dsRNA ALONE
(BINARY COMPLEX)

NEGATIVELY CHARGED
dsRNA dsRNA TERNARY COMPLEX

O = NON-POLAR RESIDUE

† = POSITIVE CHARGED RESIDUE

TOPICALLY ACTIVE COMPOSITIONS OF MISMATCHED DSRNAS

This is a Rule 62 File Wrapper Continuation of application Ser. No. 08/147,431, filed Nov. 5, 1993, now abandoned, which is a continuation of Ser. No. 07/926,372 filed Aug. 10, 1992, now abandoned, which is a continuation of Ser. No. 07/731,400 filed Jul. 17, 1991, now abandoned, which is a continuation of Ser. No. 07/545,661 filed Jul. 2, 1990, now abandoned, which is a continuation of Ser. No. 07/428,016 filed Oct. 26, 1989, now abandoned, which is a continuation of Ser. No. 07/227,929 filed Aug. 3, 1988, now abandoned, which is a continuation-in-part of Ser. No. 07/084,226 filed Aug. 12, 1987, abandoned.

This invention relates to pharmaceutical compositions for topical application containing mismatched double-stranded ribonucleic acids (dsRNAs) and biologically active fragments of mismatched dsRNAs stabilized as a ternary complex with a surfactant. The compositions are shelf stable and remain topically active as antiviral and other agents.

Nonionic surfactants (surface active agents) have proven spermicidal activity and are the active ingredients in various over-the-counter (non-prescription) contraceptive creams and foams. At high concentrations, surfactants demonstrate obvious toxic effects on cells which limit their potential utility; such concentrations are necessary for effectiveness against herpes virus since they cause disruption of the virus envelope. Surfactants have been reported to inactivate certain strains of human immunodeficiency virus (HIV), at least in vitro.

Another class of macromolecules active against viruses, cancer and inflammatory cells in vivo are dsRNAs which, while relatively non-toxic, are biologically unstable at body temperature (37° C.), which can limit their utility and ease of handling. In liquid form, certain dsRNAs must, for example, be stored carefully at 4° C. to prevent their molecular destruction. For these reasons, the dsRNAs are administered by injection into the patient's blood stream. I have now found that by preparing mixtures of surfactants and dsRNAs in physiologically acceptable carriers that I can achieve multiple unexpected properties. These new properties include: (a) stabilization of dsRNAs against temperature-associated, enzymic destruction, (b) a synergistic biological activity which actually widens the antimicrobial spectrum of the combined products as compared with either compound alone and (c) a facilitated uptake by locally available cells resulting in a higher intracellular concentration of bioactive material due to facilitated transmembrane cross-over of ternary and quaternary complexes built around a negatively charged dsRNA core molecule. Most importantly, the combined products show unusually high specific bioactivity against HIV as well as certain other venereally-transmitted pathogens including members of the herpes virus family. Thus, I describe a new series of ternary complexes (2 strands of complementary mismatched RNA plus a surfactant forming a micelle around the dsRNA) which have novel biophysical and biological properties. Alone, or with complementary lymphokines and/or inhibitors of reverse transcriptase, these products offer heightened host defense capabilities at portals of entry of various pathogens. These and other characteristics of the invention are described in more detail below.

Surface active agents used may be anionic, cationic or nonionic in nature. Typically, the effectiveness of such agents in topical uses has been attributed to their ability to dissolve various lipid-containing membranes and therein may confer their abilities to act at spermicides and to dissolve the nucleocapsid structures of herpes virus −1 and −2) see U.S. Pat. No. 4,507,281 by Asculai et al and patents cited therein which are hereby incorporated by reference.

In particular, nonionic surfactants have found considerable use in spermicides in vaginal contraceptives and one particular nonionic surfactant, designated nonoxynol-9 (NP 9), has enjoyed wide use in contraceptive creams and foams. However, care must be used in applying such surfactants as they can cause toxicity in normal cells (Asculai et al, *Antimicrob. Agents and Chemo.*, Vol 13, p. 686, 1978). Rapp et al observed a synergistic effect of human alpha interferon (a protein) with nonoxynol 9 in terms of inhibition specifically of HS-type 2 (Rapp et al, *Antimicrob. Agents and Chemo.*, Vol 28, p. 449, 1985). Also, Hicks et al (*Lancet*, Vol. 2, Dec. 21/28, p. 1442, 1985) described an in vitro inactivation of HTLV-III (HIV, formerly HIV virus) by concentrations of nonoxynol-9 (used alone), which were 0.05% or greater. Hicks also observed toxicity of nonoxynol-9 on normal lymphocytes which became pronounced at concentrations greater than 1%. It should be noted that since nonoxynol-9 concentrations in commercially-available spermicides range from 1% to 5% (Voeller, *Lancet*, Vol. 1, p. 1153, May 17, 1986), nonoxynol-9 may well damage normal genito-urinary cells while potentially attacking "free" HIV or HIV within lymphocytes. In that the development of an AIDS vaccine may be several years into the future (see Fauci, *Proc. Natl. Acad. Sci. USA*, Vol. 83, p. 9278, 1986), various steps to control spread should be implemented quickly. As Fauci points out: "a major issue centers about in whom to test the Vaccine candidate if a candidate proves safe and effective . . . even in male homosexuals . . . studies would be difficult". This underscores the importance of developing, immediately, certain topically useful procedures to lessen the risk of viral, and other microorganismal, transfer in the process of sexual relationships to prevent their further spreading to the general population. For example, Fauci estimates that the "tip of the iceberg" may be 150,000 cases (HIV) in the U.S. alone.

Topical compositions for treating viral conditions are described in the patent literature. Compositions for treating herpes simplex infections containing human interferon, an antiviral nonionic surface active agent (nonylphenoxypolyethoxyethanol) and a carrier are described in U.S. Pat. No. 4,507,281 to Asculai et al. Polynucleotides that induce interferon, such as the dsRNA polyriboinosinic acid:polyribocytidylic acid or poly I•C, are described in U.S. Pat. No. 4,283,393 to Field et al in which an interferon inducer (poly I•C) homogeneously mixed with a water soluble polymer as a controlled release topical application for the treatment of virally infected skin, eye and mucous membrane tissue susceptible to treatment with interferon. Levy in U.S. Pat. No. 4,024,241 describes nuclease-resistant hydrophilic complexes of poly I•C complexed with a poly-1-lysine and carboxymethyl-cellulose. Simple mixtures of poly I•C in aqueous solutions, ointments, creams or liquid preparations are described in U.S. Pat. No. 4,124,702 to Lampson et al.

The toxicity of poly I•C is reported in the literature (Adamson, *Nature*, Vol. 223, Aug. 16, 1969), and for this reason the therapeutic use of poly I•C has largely been abandoned. By contrast, the mismatched dsRNAs used in the pharmaceutical compositions of the present invention are relatively low or are non-toxic. Further, the inventor reports herein degradation products (fragments) of the mismatched dsRNAs, as will inevitably occur on long-term storage, remain bioactive for considerable time and in some instances are more active than the parent compound.

For completeness, it should be noted that at least two different designators for HIV virus exist; LAV is the designator for the HIV virus isolated at the Pasteur Institute, Paris, France, and HTLV-III is the designator for the HIV virus isolated at the National Institute of Health, Bethesda, Md., U.S.A. Frequently in this text, the virus will be referred to generically or designated HIV or HTLV-III or LAV without intending to differentiate between them. Furthermore, the term "HIV" in the specification and claims includes all other viruses which may be associated with producing HIV infections in man including seropositive asymptomatic carriers, AIDS-related complex or ARC and acquired immunodeficiency disease syndrome or AIDS, whether yet isolated or not.

In European Patent Application published as 0 213 921 on Mar. 11, 1987, entitled "Modulation of Virus-Related Events by Double-Stranded RNAs", the inventor describes the inhibition of HIV in human cell culture by dsRNAs, specifically using Ampligen® as a prototype dsRNA.

Cationic surface active agents are preferred surfactants; however, nonionic or anionic surfactants may also be used. Suitable anionic surfactants include sodium alkysulfonates and sodium aklybenzenesulfonates. Appropriate cationic surfactants include quaternary ammonium detergents, including cetyl pyridiuium chloride and benzoalkonium chlorides. In contrast to cationic and anionic surfactants, the nonionics contain no ionizable groups and have no molecular charge; they generally depend upon their entire molecule for surface activity.

However, almost any hydrophobic compound which has in its structure a carboxy, hydroxy, amide or amino group with a free hydrogen attached to the nitrogen can be reacted with ethylene oxide to form a nonionic detergent. In my invention, I describe the novel ternary complex of mismatched dsRNA complexed with surfactants; dsRNAs also have a hydrophobic feature which causes the nucleotide bases in the two complementary strands to form a tight double-helical structure. In my present invention, I am able to form a ternary complex, i.e., RNA Strand "1" plus (complementary_ RNA Strand "2" plus surfactant to yield a ternary (or three-membered) complex with completely novel biophysical and therapeutically important biological properties.

Figure 1:
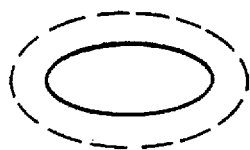
FIG. 1 is a representation of a mismatched dsRNA alone, a binary complex of two RNA strands presenting an overall negative charge on the surface of the dsRNA mass.
Figure 2:
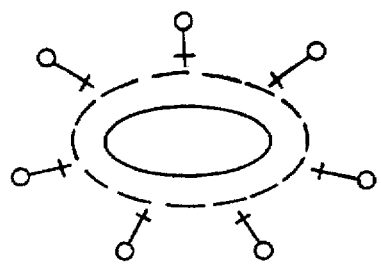
FIG. 2 is a representation of the mismatched dsRNA ternary complex (two complementary but mismatched RNA strands surrounded by a cationic surfactant) of this invention with the positively charged portion of the cationic surfactant particles oriented about the negatively charged surface of the dsRNA and the non-polar residue of the surface extending away from the dsRNA mass.

The relative concentration of the surfactant (cationic in this illustration) will control the relative polarity of the resultant complex which may vary for different therapeutic uses. By providing an excess of surfactant, once the ternary complex is formed, precipitation of the complex may result which can convey desirable properties for certain topical uses.

One key to the present invention is the building of a micelle on or around the dsRNA (as with a neutral, anionic or cationic surfactant) in order to facilitate a novel therapeutic feature—namely, high (localized) biological activity.

A micelle is defined as the structure formed by the addition of molecules with bifunctionality molecular groups to an otherwise aqueous (water compatible) substrate such as dsRNA. Bifunctionality refers, in the present context, to a molecule with one end being polar (i.e., miscible with water which is polar) and another end being non-polar (i.e., more affilic with lipids—as prime constituents of cell membranes). The desirability of building such as ternary complex which results in a micelle is that it will be more therapeutically active by virtue of two or more properties which now allow it (the resultant complex) to more readily cross the cell membranes of target cells (cancer cells, virus infected cells, immune cells, etc.):

Property 1: A key feature to facilitated transmembrane transfer is the resultant desired surface charge of the ternary (micellar) complex vs the uncomplexed (binary) dsRNA and the heightened hydrophobocity which facilitates the approach to and actual physical fusion with the cell membrane and accelerated uptake.

Property 2: The particulate nature of the ternary complexes described below (including, but not limited to the micellar complexes) will further facilitate the cellular uptake by allowing for an additional property of cellular phagocytosis which will occur minimally without micelle formation. Phagocytosis is the process whereby outpouching of cell (termed pinocytotic vacuoles, etc.) physically engulf particulate dsRNAs in ternary (or quaternary) complexes thereby accelerating their transfer to the intracellular (vs. extracellular) compartment, a necessary step to confer maximal bioactivity in man. This process of phagocytosis can also occur with biofragmented dsRNAs, e.g., mismatched dsRNAs.

The mole fraction (relative concentration) of surfactant will control relative polarity of the resultant complex which may vary for different therapeutic uses. By providing an excess surfactant once the ternary complex is formed, precipitation of the complex may result which can convey desirable properties for certain topical uses.

A special case which illustrates the utility of the present invention is the ternary a complex formed between a cationic surfactant such as cetyl trimethyl ammonium bromide (abbreviated CTAB) and dsRNA. Because of the basic nature of its polar residues, it will orient itself upon the dsRNA in such a manner that the dsRNA provides a negatively charged core around which the positive charged detergent (with its acidic groups) is deposited (see diagram). Any basic (cationic) detergent can substitute for CTAB and result in a micelle which will be much more stabilized and bioactive than, say, placing dsRNA within a simple lipid structure (e.g., liposome) which is held together only by much weaker, hydrophobic bonding. As a result, in the regulating micelle, the polar nature of the detergent has minimized the negatively charged surface of the dsRNA so that the now largely non-polar ternary complex will have facilitated transport across the cell membrane. Further specificity in uptake of the micelle may accrue by providing yet additional specificity for target cells, as by building a quaternary complex in which the fourth component provides specific tropism or attraction for a certain cell class, e.g., as by incorporating the HIV protein, gp120, to target the resultant complex to T4 lymphocyte cells, if the primary objective is to treat or prevent a retrovirus.

Presentation of the dsRNA as a ternary complex, particularly as a micelle, not only stabilizes and protects heat labile dsRNA, as explained above, it facilitates uptake of dsRNA and enriches the action of mismatched dsRNA. The micelle structure affords improved contact of the drug substance to the cell surface. The net surface charge on the micelle is more attractive and/or more compatible with most cells. In contrast, "naked" mismatched dsRNA has a high negative charge and may be physically repulsed by the cell. The dsRNA ternary complex micelle presents itself and is accepted by the cell by charge attraction. Second, the micelle structure allows the dsRNA to form particulate complexes which, in turn, affords new mechanisms of phagocytosis, as explained in detail above. Whenever a carrier/ternary complex is formed, it is inevitable that unique bioactive fragments of mismatched dsRNA will be formed and these bioactive fragments are desirable. The reason is this—ribonucleases, the chemical reason why such fragments are formed, is ubiquitous and more or less fragments will indeed be formed whatever the complex formed. The ability to form micelles with these bioactive fragments represents a critical embodiment of enhancing the utility of the invention.

There will be inevitable qualitative biophysical changes as the pharmaceutical preparation (cream, lotion or the like) sits on the pharmacist's shelf waiting to dispensed. Storage may be at $-4°$ C., $7°$ C., or at ambient temperature (usually about $20°$ C.). Far from a negative feature, these changes have been anticipated by my invention, namely: in a preferred embodiment the product begins with a core of dsRNA of the mismatched type, the object being to build a ternary or quaternary complex from this starting material. This, in practice, means that the inevitable decay of macromolecular RNA will release bioactive residual, lower molecular weight materials which will be complexes with the surfactant present to result in a slightly different micellar complexes with similar desired pharmacological properties.

Over time, the product continues to express biological therapeutic activity even though the number of RNA cores continues to decrease since the number of bioactive fragments of the dsRNA parent will continue to increase as the RNA cores are digested. Thus, the biological potency continues to be maintained or increases slightly over time as potent bioactive fragments of the dsRNA continue to be released. Thus, "stable" as used herein means the product retains therapeutic activity over time.

The nonionic surfactants of utility in my present invention can fall into at least three categories: (1) those having an ether linkage (as between hydrophilic and hydrophobic portions of molecules) such as polyoxyethylene alcohols, polyoxyethylene esters of fatty acids, polyoxyethylene aklylphenols or mercaptans or alkyl amines; (2) those having an ester or ether-ester linkage; and (3) those having a amide linkage. Ionic detergents can also be used as I describe elsewhere in the application, particularly in the formation of novel micelles which result in rapidly achieved, high intracellular concentrations of dsRNAs and bioactive fragments thereof. Ether or amide linkages are preferred embodiments in the context of the present inventions, and some examples are: nonoxynol-9 (nonylphenoxypolyethoxy ethanol); Triton-100 (p-diisobutylphenoxypolyethyoxy ethanol); polyoxyethylene oleyl ether (also called Brij 97); and Onyx-OL (also called Onyx-OL 345). In the inventions I describe below, the amount of surfactant employed varies between 0.01% and 20%, although the preferred range is below 12% by weight, the final formulation being a function also of the relative mismatched dsRNA content as well as the therapeutic objective (e.g., chlamydia being somewhat more resistant to the ternary complex than HSV-2) and particular form of pharmaceutical presentation. Preferably, the amount of mismatched dsRNA ranges from about 0.001 to about 10 weight percent of the composition or more depending upon the particular formulation (solubility of dsRNA is not a limiting factor in suspensions, for example) and the condition(s) the product is intended to treat. When dsRNA fragments are used, the upper limit of concentration may be somewhat high because any solubility constraints have been lifted. Whatever the relative content of dsRNA to surfactant in the formulation, the balance of the pharmaceutical composition can generally be comprised simply of an inert, physiologically compatible, pharmaceutically acceptable carrier.

Background on dsRNAs. I recently described this field historically (Carter et al, *J. Biol. Resp. Modifiers*, Vol. 4, articles beginning at p. 495–613 which are herein incorporated by reference). dsRNAs were largely overlooked clinically as potential anticancer and antiviral drugs because of the many clinical toxicities and lack of efficacy associated with the first clinically tested dsRNA-polyinosinic•polycytidylic acid (poly I•C or $rI_n•rC_n$). However, I showed earlier that mismatching dsRNA helices, which causes much less induction of tumor necrosis factor (TNF) a highly toxic lymphokine (protein) leading to cachexia, improved both the therapeutic activity as well as reduced toxicity. Indeed, dsRNA is more active than interferon against various tumors and viruses including HIV (Carter et al, *Lancet*, Jun. 6, 1987 and references cited therein). However, the pharmacologic "formulation" and storage of mismatched dsRNA, the form of dsRNA with the most favorable therapeutic ratio to date in human studies, has proven to be a cumbersome feature or obstacle which feature I am able to overcome in the context of my present invention. Data indicate that once mismatched dsRNA is placed in an aqueous solution, it must be injected into a recipient human or animal within 4 hours or be discarded. This "rapid use of discard" step is necessary because the drug at temperatures about $4°$ C. consistently undergoes gradual degradation, in part due to the prevalence of various RNases, i.e., enzymes which degrade dsRNA to which mismatched dsRNAs are particularly susceptible. Such enzymes are ubiquitous in nature, and thus are present on hand, saliva, within sterile water, on glassware, etc. Accordingly, the only modus operandi—until the present invention as herein described—to preserve safely mismatched dsRNA products as freeze-dried (lyophlized) powders.

In the present invention, I have effectively leapt over this long-standing obstacle by the formation of a novel set of ternary complexes with greatly enhanced stability at various ambient temperatures. Mismatched dsRNAs are vulnerable to nuclease attack, yet surrounded by and complexed with the surface (forming a ternary complex), degradation products of the dsRNA remain active, often more active than the parent compound, as described below.

In another article I recently published (Brodsky, Carter et al, *J. Biol. Res. Mod.*, Vol. 4, p. 669, 1985); see especially FIG. 1, p. 673, I note that (a) RNase inhibitors must even be added to any tubes into which mismatched dsRNA samples are introduced during lability/instability, and (b) dsRNA stability in vivo is very brief, being measured in terms of only minutes. Indeed, the T½ (half-life) of injected dsRNA (e.g., $rI_n•r(C_{11-14},U)_n$ also called Ampligen®, a trademark of HEM Research, Inc.) has an estimated T½ in human serum of 20 minutes±15 minutes. Different human subjects will have varying amounts of hydrolytic enzymes, as I have noted in my previous studies on this subject; all humans which I have studied to date (approximately 115 individuals) have significant levels of enzymes (endo- or exonucleases) which degrade dsRNA rapidly.

This invention is a topically applied pharmaceutical composition for the treatment of conditions susceptible to or sensitive to treatment with mismatched dsRNA, such as viral infections, skin cancer and the like, in which the dsRNA is topically applied in bioactive form. The normally heat labile mismatched dsRNA is presented in a ternary complex of two strands of the RNA, mismatched as defined herein, complexed with an anionic, nonionic or cationic surfactant or detergent. Often the active component forms a micelle with the surfactant and may be present as the parent compared (mismatched dsRNA) or as bioactive fragments of the parent compound.

Conditions treated by the topical compositions of this invention include those known to be sensitive to mismatched dsRNA therapy and those conditions for which mismatched dsRNA provides a unique means of administration. These conditions include, but are not limited to, (1) human retroviruses infections including HIV, (2) members of the herpes virus family, e.g., herpes simplex and herpes zoster; (3) cytomegalovirus or CMV (sometimes classified as a herpes-type virus), (4) localized skin cancer with and without vital etiology, (5) susceptible sexually transmitted viral conditions and venereal infections including chalmydia (many of the conditions listed above are sexually transmitted), and (6) venereal infections in which the causative viral agent is primary or secondary to another venereal infection itself insensitive or less than adequately controlled by mismatched dsRNA which secondary infection is being treated by another therapeutic modiality (such as a concurrent gonorrheal infection for which the patient is receiving tetracycline therapy).

The compositions of this invention include pharmaceutical presentations such as liquids—solutions such as isotonic eyedrops and nosedrops or sprays, lotions, creams, foams, gels and viscous fluids, including lubricants well tolerated by the genito-urinary system and/or spermicides well tolerated by the genito-urinary system; solid and semi-solid preparations—ointments, opthalmic ointment or cream, creams, salves, suppositories (both rectal and vaginal), sticks such as lipsticks used to treat herpes simplex lesions, and eye inserts.

By "mismatched dsRNAs" are meant those in which hydrogen bonding (base stacking) between the counterpart strands is relatively intact, i.e., is interrupted on average less than one base pair in every 29 consecutive base residues. Mismatching is an interruption of the normal geometry of the RNA double helix by in-pouching (or out-pouching) of the strands which represent points of vulnerability of the dsRNA to digestion by ribonucleases. The term "mismatched dsRNA" should be understood accordingly.

The dsRNA may be a complex of polyinosinate and a polycytidylate containing a proportion of uracil bases or guanidine bases, e.g., from 1 in 5 to 1 in 30 such bases (poly I. poly ($C_{4-29}$x>U or G).

The dsRNA may be of the general formula $rI_n.(C_{12}U)_n$. Other suitable examples of dsRNA are discussed below.

In the preferred mismatched dsRNA, $rI_n \cdot (C_{12}, U)_n$, a region consisting of an uninterrupted stretch of 6 to 12 base pairs, i.e., one-half to one full turn of an RNA helix, serves both as a biotrigger causing release of lymphokines and as an obligate intracellular co-factor for enzymes comprising the natural antiviral pathways. The mismatched regions consisting of uracil residues is periodically inserted in the polypyrimidine strand to accelerate dsRNA hydrolysis and thus prevent toxicity.

The mismatched dsRNAs preferred for use in the present invention are based on copolynucleotides selected from poly ($C_n$,G) in which n is an integer having a value of from 4 to 29, and are mismatched analogs of complexes of polyriboinosinic and polyribocytydilic acids, formed by modifying $rI_n.rC_n$ to incorporate upaired bases (uracil or guanidine) along the polyribocytidylate ($rC_n$) strand. Alternatively, the dsRNA may be derived form poly (I). poly (C) dsRNA by modifying the ribosyl backbone of polyriboinosinic acid ($rI_n$) e.g., by including 2'-O-methyl ribosyl residues. These mismatched analogs of $rI_n.rC_n$, preferred ones of which are of the general formula $rI_n.r(C_{11-14},U)_n$ and $rI_n.r(C_{29},G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

Other examples of mismatched dsRNA for use in the invention include:

poly (I)•poly ($C_4$,U)
poly (I)•poly ($C_7$,U)
poly (I)•poly ($C_{13}$,U)
poly (I)•poly ($C_{22}$,U)
poly (I)•poly ($C_{20}$,G)
poly (I)•poly ($C_{29}$,G) and
poly (I)•poly ($C_p$)$_{23}$ G>p The invention can be practiced by adding another lymphokine to the ternary complex—the purpose of this additive being to modulate further the number and nature of the cells available for reaction with topically applied dsRNA. For example, the addition of interleukins to the ternary complex will provide for further recruitment of T-lymphocytes as well as the potential for synergistic therapeutic interplay with dsRNA. Similar rationales for added utility may come from combinations with other lymphokines such as, but not limited to, interferons and tumor necrosis factors. These lymphokines might be of special utility in the treatment of topical cancers and certain viral infections. In some instances, specific viral inhibitors such as azodithymidine or gangcyclovir may also be added.

To illustrate the potential for resultant quaternary complexes, I prepared pharmaceutical lotion (designated A in the text) which contained 5,000–20,000 units of IL-2 and 10 mg of dsRNA. I applied generous portions of the lotion to the skin of athymic (hairless) mice immediately over the area into which was previously infected human melanoma (skin cancer) cells. Untreated, such subcutaneously injected tumor cells grow such that eventually the animal is cosmetically disfigured by the tumor mass. However, animals which received the IL-2/dsRNA/surfactant lotion showed rapid tumor regression and thrived over their untreated counterparts.

I was also able to document a systemic effect of this regimen by analyzing immune cell subpopulations in their spleens using the technique of flow cytometry whereby specific numbers of immunologicallay-relevant cells can be determined. When compared to non-treatment, the increments were: NK (natural killer) cells—63% dsRNA alone vs. 87% by combination with interleukin-2 [antibody marker used in flow cytometry machine was ASGMI]; LAK (lymphokine-activated killer) cell—228% dsRNA alone vs. 412% by combination with interleukin-2 [antibody marker used in flow cytometry was Thy 1.2]; and lymphocyte T4 cells—no significant increment by dsRNA alone vs. 263% by combination with interleukin-2 [antibody marker used in flow cytometry was L3T4]. As a negative control, I noted that none of the lotions applied topically affected the number of lymphocyte T8 (suppressor) cells as measured in the spleen.

As discussed herein, lymphokines will be able to include the interferons, preferably interferon alpha, the interleukins, specifically interleukin-2 (IL-2) and recombinant interleukin-2 (rIL-2), and tumor necrosis factor (TNF). Also included are lymphokine activated killer (LAK) cells formed in animals in response to exposure to a lymphokine. Inhibitors of reverse transcriptase, such as 3'-azido-3'-deoxythymidine (AZT) may be included in the formulations in addition to or instead of a lymphokine.

When interferon (alpha) is used as the lymphokine, an amount of from 0.01 to 100,000 IRU per milliliter of the patient's body fluid is provided. When IL-2, preferably rIL-2, is the lymphokine, the amount administered lies within a range of about $10^2$ IL-2 units per kg of the patient's body weight up to a value approaching unacceptable levels of toxicity in that patient, which may be as high as $10^6$ IL-2 units. However, most effective, toxic-reaction manageable values are in the range of from about $10^3$ to about $10^4$ IL-2 per kg of body weight.

The usual amounts of dsRNA administered provide a level of from 0.1 to 1,000 micrograms dsRNA per milliliter of the patient's body fluid. The term body fluid is intended to refer to that solution of serum, salts, vitamins, etc., which circulates within the organism and bathes the tissues. When both agents (dsRNA and a lymphokine and/or inhibitor of reverse transcriptase) are administered they are usually administered as a mixture, but may be administered separately but simultaneously, or sequentially.

Administration of a dsRNA and a lymphokine "in combination" includes presentations in which both agents are administered together as a therapeutic mixture, and also procedures in which the two agents are administered separately but simultaneously. Administration "in combination" further includes the separate administration of one of the drugs in which one of the drugs is given first followed shortly by the second.

I have observed a previously undetected biochemical anomaly in which a key enzyme (RNase L) associated with the body defense mechanisms against both cancer and viral diseases is operating in an accelerated and apparently uncontrolled manner. These and other observations are described in my copending application Ser. No. 074,649 filed Jul. 17, 1987, and entitled "Double-Stranded RNA Correction of Aberrant Metabolic Pathways Associated With Uncontrolled Tumor Cell and Virus Growth Cycles", the disclosure of which is hereby incorporated by reference. In separate experiments, I compared the relative abilities of these two different cells (cells with abnormal RNase L) to withstand viral challenge. I observed that the titers (yield) of progeny retroviruses were significantly higher in those cells with the abnormal RNase L activity which generated NCP so rapidly.

Double-stranded RNAs, especially mismatched dsRNAs, restore normalcy of RNase L kinetics and degradation products as reported in my U.S. patent application of Jul. 17, 1987, noted above. Further, the rate of restoration of normalcy by double-stranded RNA can be accelerated by prior exposure to lymphokines.

In the experiments described below, dsRNAs were first reconstituted from lyophilized (freeze-dried) powders and then mixed with solutions of various surfactants with emphasis on the use of nonionic surfactants. In some experiments, I used an inert carrier especially if the objective was to apply the resultant complex to a surface or biological cavity, etc. The dsRNA/surfactant complex was incubated overnight and the mixture then diluted with a standard medium saline solution for some of the assays described in Tables 1 and 2.

It will be recognized that these new pharmaceutical compositions may be administered topically by a great variety of methods. For example, the compositions may be delivered to the affected region, or the region not yet affected but delivered in a prophylactic mode, in microencapsulated form, such as the use of lipid or lipid-like vesicles. They may also be delivered as a foam, spray, tampon, vaginal or rectal suppository, or directly into and onto a condom during manufacture. The latter (condom introduction) would not have been possible without this invention which now allows prolonged stability and continued bioactivity of mismatched dsRNA or biologically active fragments thereof at ambient temperatures (20° C.–23° C.) and a reliable product shelf life. For example, the present invention can be readily practiced by inserting the dsRNA/surfactant complex using the mechanical process described by Reddy in U.S. Pat. No. 4,415,548 describing the manufacture a lubricated spermicidal male contraceptive.

In particular, the present inventions also overcome some of the undesirable effects of certain spermicides such as the popular nonoxynol-9 (nonylphenoxypolyethoxyethanol), because my discovery allows the effective concentration of nonoxynol-9 to be reduced at least for certain indications, as discussed in more detail below (see Table 2). Vaginitis as well as placental necrosis and embryotoxic potential has been documented with this spermicide (Tryphones et al, *Toxicology*, Vol. 39 (2), May, p. 177, 1986). I conducted similar experiments with other spermicides including aryl-4-guanidinobenzoates (NPGB) inhibitors of sperm acrosin, an enzyme with an essential function in the fertilization process; such NPGB molecules being capable of synthesis from FDA-approved phenols as described by Kaminski et al *J. Med. Chem.* (Apr) Vol. 29 (4), p. 514, 1986). Other spermicides compatible with my present invention include chlorhexidine diacetate (described by Sharman et al, *Fertil. Steril.*, Vol. 45 (2) Feb., p. 259, 1986); menfegol (see Lamptey et al, *Contraception*, Vol. 32(5), Nov. p. 445, 1985); benzalkonium chloride (not absorbed through the vaginal wall like nonoxynol-9 as described by Zufferey, *J. Gynecol. Obstet. Biol. Reprod.* (Paris) Vol. 14(3), p. 359, 1985); and the more recently described two-phase nonoxynol-9 system in which a lubricant system contains silicon fluid plus nonoxynol-9 plus a spermicidal cream (see Rodgers-Meame et al, *Fertiliz. Steril.* Vol. 43(6), June, p. 931, 1985). In the latter case, it is apparent that approximately 2.0 mg of dsRNA can be added to either (or both) the lubricant system consisting of 0.45±0.1 ml of silicon fluid containing 6.6%±0.5% surfactant or the spermicidal cream base consisting of 0.45±0.1 ml made of polyethylene glycol 400 (approximately 63%) and polyethylene glycol 3350 (approximately 30%). The above are simply non-limiting examples of the compatibility of my invention as an adjunct to various contraceptive modes.

Importantly, the pharmaceutical compositions I describe display both antimicrobial as well as antiviral activity (see Table 2 for an example), While this is also stated to be feasible in Asculai and Rapp in U.S. Pat. No. 4,507,281, (in which they combine interferon with nonoxynol-9), the present facts are that interferons, alone or mixed with such surfactants, are relatively inert against many viruses, especially the human immunodeficiency viruses. There is no suggestion of a novel macromolecular aggregate such as I describe with a dramatic shift in both biological properties and concomitant shift in certain biophysical properties. While I observed an increase in apparent molecular weight of the ternary complexes by using low angle laser light scattering (and correcting to $S_{20}W$ by use of the studier equation), I found no change in apparent molecular weight during analytical ultra centrifugation possibly because the "drag" effect of the new hydration shells of the ternary complex offset the apparent increase in mass.

Tables 1 and 2 show typical results of my invention. The results are extraordinarily dramatic both in terms of new biophysical properties (increased thermal stability of ternary complexes) and new biological properties (widened antiviral and antimicrobial range).

TABLE 1

Stabilization of Biophysical and Biochemical Properties of dsRNA Complexed With Surfactants

| Formulation/ Concentration | Time @ 37° C.[1] (in 25% Human Sera) | Mol. Wt. (est.)[2] ($S_{20}W$) | Spec. Activity[3] (2'—5' oligo A Synthesis) in % |
|---|---|---|---|
| 1. Mismatched dsRNA | 0 | 10.5 | 100 |
| (2.5 mg/ml) | 1 hr. | 6.3 | 90 |
| | 6 hr. | 2.1 | <5 |
| | 24 hr. | Not detectable | <3 |
| | 48 hr. | Not detectable | <3 |
| | 72 hr. | Not detectable | <3 |
| | 90 hr. | Not detectable | <3 |
| 2. Mismatched dsRNA | 0 | 10.5 | 100 |
| (2.5 mg/ml) plus | 1 hr. | 10.5 | 100 |
| nonylphenoxy- | 6 hr. | 10.0 | 100 |
| polyethoxy ethanol | 24 hr. | 8.3 | 90 |
| (nonoxynol-9 at | 48 hr. | 4.5 | 40 |
| 1% in physiol. | 72 hr. | 3.0 | 25 |
| buffer) | 90 hr. | Not detectable | <3 |
| 3. Mismatched dsRNA | 0 | 10.5 | 100 |
| (2.5 mg/ml) plus | 6 | 10.0 | 95 |
| polyoxyethylene | 24 hr. | 8.5 | 8.8 |
| oleyl ether (1%) | 48 hr. | 6.0 | 70 |

Legend:
[1]Pooled Human Sera from normal volunteers was used as a source of endo- and exo-nucleolytic enzyme;
[2]mol. wt. determinations as previously described (Carter et al, J. Mol. Biol., Vol. 70, p. 567, 1972);
[3]oligo 2'–5' A Synthetase induction measured in deploid human fibroblast cell extracts using poly I'C as a control (100%) as previously described (Carter et al, J. Biol. Resp. Mod., 4, p. 613, 1985)

TABLE 2

Formulation of dsRNA/Surfactants Complexes Widens the Therapeutic Spectrum Against Pathogens Including Viruses

| Formulation | Concentration | HIV Titer[1] | HSV-2 Titer[2] | Chlamydia[3] (number of elementary bodies) |
|---|---|---|---|---|
| 1. dsRNA | 0 micrograms | $1 \times 10^6$ | $5 \times 10^6$ | 108 |
| | 10 micrograms | $5 \times 10^5$ | $3 \times 10^6$ | 105 |
| | 30 micrograms | $1 \times 10^5$ | $5 \times 10^4$ | 105 |
| | 50 micrograms | $1 \times 10^3$ | $2 \times 10^4$ | 95 |
| | 200 micrograms | <10 | $8 \times 10^3$ | 80 |
| 2. Nonoxynol-9 | 0 percent | $1 \times 10^6$ | $5 \times 10^6$ | 110 |
| | 5 percent | $3 \times 10^3$ | $3 \times 10^3$ | 110 |
| | 1 percent | $3 \times 10^3$ | $4 \times 10^5$ | 110 |
| | 0.05 percent | $2.5 \times 10^3$ | $8 \times 10^5$ | 108 |
| | 0.01 percent | $3 \times 10^3$ | $5 \times 10^6$ | 110 |
| 3. dsRNA/nonoxynol-9 | 0 | $1 \times 10^6$ | $5 \times 10^6$ | 108 |
| | 30 microgram/5% | <10 | $1 \times 10^1$ | 20 |
| | 30 micrograms/1% | <10 | $2 \times 10^2$ | 25 |
| | 30 micrograms/0.05% | <10 | $1 \times 10^3$ | 40 |
| | 30 micrograms/0.01% | <10 | $5 \times 10^2$ | 55 |

Legend:
[1]An $ID_{50}$ assay was used as described by Hicks (ref. cited above). Briefly, a microculture system was used to titrate infections HIV following exposure to peripheral blood cells of normal individuals in the presence or absence of formulations cited; cultures were terminated at 21 days and supernatant fluids harvested and measured for HIV reverse transcriptase by standard methodology.
[2]HS-2 was measured in confluent HEL cells using plaque formation after methylcellulose overlay (Rapp et al, Antimicrob. Agents and Chemo. Vol. 28, p. 449, 1985).
[3]An elementary body assay was used employing quantitation in McCoy cell monolayers in 96-well microtiter plates; standardized inocula containing known numbers of inclusion forming units/ml were added to each well and incubated for 60 minutes with the various formulations (Kappres et al Sexually Transmitted Diseases, Vol. 13, p. 134, 1986).

The following are typical examples of suitable formulations containing a nonionic surfactant[1,2,3] and dsRNA:

| | | |
|---|---|---|
| Pharmaceutical Cream A | | |
| purified water | 41.00 | grams |
| crystalline wax | 3.00 | grams |
| lanolin | 10.00 | grams |
| petrolatum | 41.00 | grams |
| sorbitan monooleate | 4.75 | |
| polysorbate 80 | 0.25 | grams |
| dsRNA | 10–180 | mg. |
| Pharmaceutical Lotion | | |
| purified water | 7.00 | ml. |
| oleic acid | 1.50 | grams |
| polyethylene glycol monostearate | 10.50 | grams |
| Carbopol-934 | 42.25 | |
| propylene glycol | 24.75 | ml. |
| triethanolamine | 1.00 | ml. |
| silicon fluids | 10.00 | ml. |
| dsRNA | 10–180 | mg. |
| Pharmaceutical Cream B | | |
| Spermaceti | 7.5% | |
| wax | 12.0% | |
| mineral oil | 56.0% | |
| sodium borate | 0.5% | |
| sorbitan monooleate | 5.0% | |
| water | 19.0% | |
| dsRNA | 1–200 | mg. |

Types of surfactants used are as follows: [1] typical ester or ether-ester linkages such as sorbitans (mono or tri-stearates), sorbitan monooleates, sesquioleates, triooleates, polyoxyethylene, sorbitan monolaurate, sorbitan monopalmitate. [2] typical ether-amide linkages such as fatty alkanolamides, including onyx-ol, unamide, monoamine and lauric diethanolamide such as polysorbate 20, polysorbate 80, onyx-ol, p-diisobutylphenoxyl-polyethoxy-ethanol, nonylphenoxypolyethoxy ethanol, polyoxyethylene oleyl ether, etc. [3] ether linkages are described in text and include polyoxyethylene alkyl-phenols, polyoxyethylene alcohols, polyoxyethylene esters of fatty acids, polyoxyethylene mercaptans and polyoxyethylene alkyl amines, etc.

I also evaluated more complex compositions including those containing lymphokines or dsRNA-related mediator substances to determine their compatibility with the present inventions. Specifically, I introduced into the topical preparations, in this case lotions, interferons and/or certain 2'–5'A core molecules including three 2,5-phosphorothioate trimer cores with RpRp, SpRp and RpSp internucleotide linkages which I have recently shown to activate the RNase L associated with intracellular host defense pathways. Such products with suitable vectors, such as unilamellar liposomes, monoclonal antibodies, reconstituted viral envelopes, etc., could be delivered intracellularly to provide an additional layer of antiviral, immunological and anticancer properties.

What is claimed is:

1. A topically applied pharmaceutical composition for the treatment of a condition susceptible to or sensitive to treatment with mismatched dsRNA comprising in a pharmaceutically acceptable topical carrier an effective quantity of a mismatched dsRNA in a ternary complex of two mismatched strands of dsRNA complexed with a surfactant.

2. The topically applied pharmaceutical composition of claim 1 in which the ternary complex is a micelle in which the mismatched dsRNA is surrounded by the surfactant.

3. A spermicidal and anitvirally-active topical pharmaceutical composition comprising a spermicidally effective amount of a spermicide and from 0.001 to 10 weight percent of a mismatched dsRNA calculated on the total weight of the composition in a pharmaceutically acceptable carrier.

4. The spermicidal and antivirally-active topical pharmaceutical composition of claim 3, further including a lubricant non-irritating to the human genito-urinary tract.

5. A condom coated with the pharmaceutical composition of claim 3 or 4.

6. A method of treating viral infections of the skin, eye and mucous membrane tissue susceptible to treatment with mismatched dsRNA comprising topically applying to viral-affected skin, eye or mucous membrane tissue a therapeutically effective amount of mismatched dsRNA in a stabilized topical pharmaceutical composition in which the mismatched dsRNA forms a ternary complex of two mismatched strands of RNA complexed with a surfactant.

7. A composition of claim 1 in which the amount of dsRNA is about 0.001 to 10 weight percent of the overall composition and the amount of surface active agent is from 0.005 to 20% by weight of said overall composition.

8. A composition of claim 1, in which the mismatched dsRNA is a complex of polyinosinate and a polycytidylate containing from 1 in 5 to 30 uracil or guanidine bases.

9. The composition of claim 1, in which the dsRNA contains regions of bond breakage and the dsRNA exhibits the favorable therapeutic ratio property of $rI_n \cdot r(C_{11-14},U)_n$.

10. The composition of claim 1, in which the dsRNA is $rI_n \cdot r(C_{11-14},U)_n$.

11. The topically applied pharmaceutical composition of claim 1 in which the mismatched dsRNA ternary complex has the structure as depicted in FIG. 2.

12. The topically applied pharmaceutical composition of claim 1 wherein the surfactant comprises cetyl trimethyl ammonium bromide.

13. The topically applied pharmaceutical composition of claim 1 wherein the surfactant comprises nonylphenoxypolyethoxy ethanol.

14. A topically pharmaceutical composition comprising from about 0.001 to about 10 weight percent of $rI_n \cdot r(C_{11-14},U)_n$ in a pharmaceutically acceptable carrier.

15. The topical pharmaceutical composition of claim 14 further including from abut 0.01 weight percent to about 20 weight percent of a non-ionic surfactant.

* * * * *